US012799061B2

(12) United States Patent
Tanizaki et al.

(10) Patent No.: US 12,799,061 B2
(45) Date of Patent: Nov. 17, 2026

(54) METHOD FOR PRODUCING FORM-II TYPE REDUCED COENZYME Q10 CRYSTAL OR CRYSTALLINE SOLID OF SAME, AND CRYSTALLIZING APPARATUS

(71) Applicant: KANEKA CORPORATION, Osaka (JP)

(72) Inventors: Subaru Tanizaki, Takasago (JP); Tadao Ono, Takasago (JP); Takanori Hashimoto, Takasago (JP)

(73) Assignee: KANEKA CORPORATION, Osaka (JP)

( * ) Notice: Subject to any disclaimer, the term of this patent is extended or adjusted under 35 U.S.C. 154(b) by 531 days.

(21) Appl. No.: 18/283,863

(22) PCT Filed: Mar. 4, 2022

(86) PCT No.: PCT/JP2022/009362

§ 371 (c)(1), (2) Date: Sep. 25, 2023

(87) PCT Pub. No.: WO2022/202215

PCT Pub. Date: Sep. 29, 2022

(65) Prior Publication Data

US 2024/0166589 A1 May 23, 2024

(30) Foreign Application Priority Data

Mar. 26, 2021 (JP) ................................ 2021-053784

(51) Int. Cl.
*C07C 45/81* (2006.01)
*B01D 9/00* (2006.01)
*C07C 46/10* (2006.01)

(52) U.S. Cl.
CPC ............ *C07C 45/81* (2013.01); *B01D 9/0036* (2013.01); *B01D 2009/0086* (2013.01); *C07B 2200/13* (2013.01)

(58) Field of Classification Search
CPC ......... C07C 45/81; C07C 46/10; C07C 50/28; C07B 2200/13; B01D 9/0036
See application file for complete search history.

(56) References Cited

U.S. PATENT DOCUMENTS

| | | | |
|---|---|---|---|
| 6,184,255 B1 | 2/2001 | Mae et al. | |
| 2004/0197886 A1 | 10/2004 | Ueda et al. | |
| 2004/0214301 A1 | 10/2004 | Ueda et al. | |
| 2014/0120073 A1 | 5/2014 | Kawachi et al. | |
| 2021/0317057 A1 | 10/2021 | Yamaguchi et al. | |

FOREIGN PATENT DOCUMENTS

| | | | |
|---|---|---|---|
| JP | 10-109933 | A | 4/1998 |
| JP | 2003-89669 | A | 3/2003 |
| JP | 2008-195650 | A | 8/2008 |
| WO | WO 03/006409 | A1 | 1/2003 |
| WO | WO 03/006411 | A1 | 1/2003 |
| WO | WO 2012/176842 | A1 | 12/2012 |
| WO | WO 2020/045571 | A1 | 3/2020 |

OTHER PUBLICATIONS

International Search Report (PCT/ISA/210), issued in PCT/JP2022/009362, dated Apr. 19, 2022.

Extended European Search Report for European Application No. 22775011.4, dated May 9, 2025.

Moscosa-Santillan et al., "Study of batch crystallization and determination of an alternative temperature-time profile by on-line turbidity analysis—application to glycine crystallization," Chemical Engineering Science, vol. 55, No. 18, XP027211202, Sep. 15, 2000, pp. 3759-3770.

*Primary Examiner* — Sikarl A Witherspoon
(74) *Attorney, Agent, or Firm* — Birch, Stewart, Kolasch & Birch, LLP

(57) ABSTRACT

It is an object of the present disclosure to provide a method for producing a reduced coenzyme Q10 Form II crystal or a crystalline solid thereof, which is capable of stably producing a reduced coenzyme Q10 Form II crystal or a crystalline solid thereof.

The present embodiment is a method for producing a reduced coenzyme Q10 Form II crystal or a crystalline solid thereof, the method using a crystallizer provided with a crystallization unit, a turbidity detection unit capable of detecting a turbidity in the crystallization unit, and a temperature adjustment unit capable of adjusting a temperature in the crystallization unit, and the method including: accommodating a mixed solution containing an alcohol and a reduced coenzyme Q10 in the crystallization unit; adding a reduced coenzyme Q10 Form II crystal as a seed crystal to the mixed solution; and precipitating a reduced coenzyme Q10 Form II crystal in the mixed solution after adding the seed crystal, wherein the precipitation includes controlling a temperature with the temperature adjustment unit based on a turbidity change rate obtained by the turbidity detection unit.

14 Claims, 1 Drawing Sheet

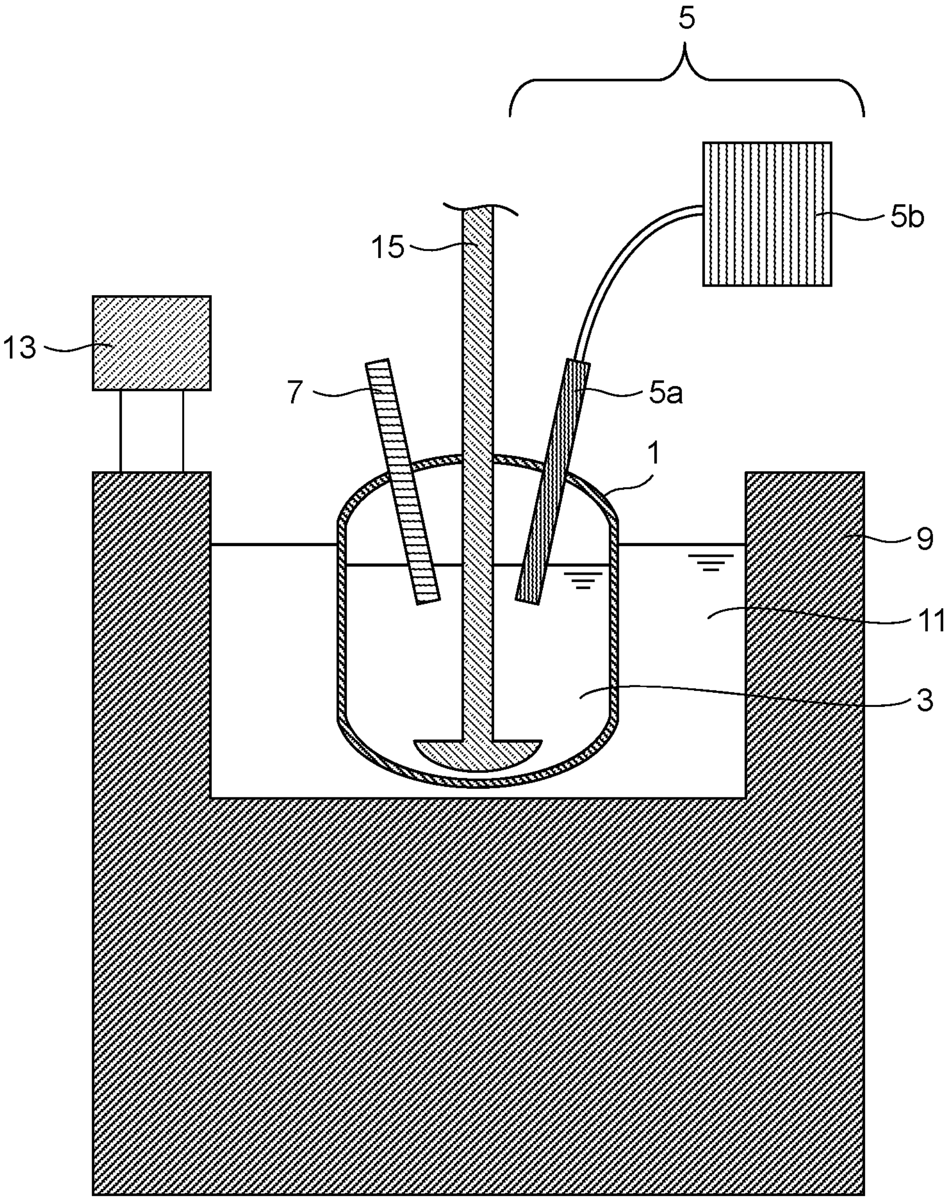
5
5b
15
13
7
5a
1
9
11
3

METHOD FOR PRODUCING FORM-II TYPE REDUCED COENZYME Q10 CRYSTAL OR CRYSTALLINE SOLID OF SAME, AND CRYSTALLIZING APPARATUS

TECHNICAL FIELD

The present disclosure relates to a method for producing a reduced coenzyme Q10 Form II crystal or a crystalline solid thereof, and a crystallizer.

BACKGROUND ART

Coenzyme Q is an essential component widely distributed in living organisms from bacteria to mammals, and is known as a member of mitochondrial electron transfer system in cells in the living organisms. Coenzyme Q engages in electron transfer in the electron transfer system by the repetition of oxidation and reduction in mitochondria. Further, reduced coenzyme Q is known to have antioxidant activity. The major component in humans is coenzyme Q10 which is one having 10 repeating structures in the side chain of coenzyme Q, and usually, about 40% to 90% thereof is present in the living body as the reduced form. The physiological activity of coenzyme Q includes activation of energy production by mitochondrial activation, activation of cardiac function, an effect of stabilizing cell membranes, and an effect of protecting cells by antioxidant activity.

While coenzyme Q10 currently produced and sold is, in large part, oxidized coenzyme Q10, reduced coenzyme Q10 which exhibits higher oral absorbability than that of oxidized coenzyme Q10 has also been commercially available and has come to be used in recent years.

A common method for obtaining reduced coenzyme Q10 has already been disclosed (Patent Literature 1). Furthermore, several methods for obtaining reduced coenzyme Q10 as a crystal have also been known. For example, a method of crystallizing reduced coenzyme Q10 in an alcohol solution and/or a ketone solution to produce a crystal (Patent Literature 2), a method of adding a high concentration liquid phase of reduced coenzyme Q10 into a poor solvent for crystallization (Patent Literature 3), and the like have been reported.

On the other hand, Patent Literature 4 reports that crystal polymorphism is found in reduced coenzyme Q10. It has been reported that a newly appearing crystal form (wherein this crystal is hereinafter referred to as a "reduced coenzyme Q10 Form II crystal or Form II crystal") is much more stable than the conventional reduced coenzyme Q10 (wherein this crystal is hereinafter referred to as a "reduced coenzyme Q10 Form I crystal or Form I crystal") and also, is excellent in other physical properties. In addition, Patent Literature 5 reports a method for producing a reduced coenzyme Q10 Form II crystal. Patent Literature 5 discloses a method for producing a reduced coenzyme Q10 Form II crystal, which comprises: adding a reduced coenzyme Q10 Form II crystal as a seed crystal to a solution with a temperature of 32° C. to 43° C., containing at least one organic solvent selected from the group consisting of an alcohol, a hydrocarbon, an aliphatic acid ester and a nitrogen compound, and reduced coenzyme Q10, to prepare a mixed solution; and precipitating a reduced coenzyme Q10 Form II crystal in the mixed solution, in claim 1.

CITATION LIST

Patent Literature

Patent Literature 1: JP Patent Publication No. H10-109933 A

Patent Literature 2: WO2003/006409

Patent Literature 3: JP Patent Publication No. 2003-089669 A

Patent Literature 4: WO2012/176842

Patent Literature 5: WO2020/045571

SUMMARY OF INVENTION

Technical Problem

Patent Literature 4 discloses a method for obtaining a reduced coenzyme Q10 Form II crystal, in which crystallization is carried out under specific conditions. However, there is a case where it takes a long period of time and the recovered amount is small. Thus, it cannot be necessarily said that this method is industrially optimal. The method disclosed in Patent Literature 5 is intended to provide an efficient production method for obtaining a reduced coenzyme Q10 Form II crystal, wherein the production method is also suitable for production in an industrial scale, which focuses mainly on temperatures.

The present inventors made intensive studies on a method for producing a reduced coenzyme Q10 Form II crystal or a crystalline solid thereof and accordingly found that when controlling the precipitation of a reduced coenzyme Q10 Form II crystal exclusively based on temperature, even in a case in which a reduced coenzyme Q10 Form II crystal is repeatedly produced under the same temperature conditions, there is a significant lot difference in oxidation stability of the resulting reduced coenzyme Q10 Form II crystal or a crystalline solid thereof.

The present inventors made studies on a method for producing a reduced coenzyme Q10 Form II crystal or a crystalline solid thereof with a focus on factors other than temperatures and accordingly found that a reduced coenzyme Q10 Form II crystal or a crystalline solid thereof can be stably produced by controlling the temperature based on turbidity change rate. Accordingly, it is an object of the present disclosure to provide a method for producing a reduced coenzyme Q10 Form II crystal or a crystalline solid thereof, which is capable of stably producing a reduced coenzyme Q10 Form II crystal or a crystalline solid thereof. It is another object of the present disclosure to provide a crystallizer that can be used when carrying out a method for producing a reduced coenzyme Q10 Form II crystal or a crystalline solid thereof.

Solution to Problem

When precipitating a reduced coenzyme Q10 Form II crystal in a mixed solution containing alcohol and reduced coenzyme Q10, as the precipitation proceeds, the amount of the reduced coenzyme Q10 Form II crystal in a mixed solution increases, resulting in increased turbidity. The present inventors found that by controlling the temperature based on the turbidity change rate, it is possible to stably produce a reduced coenzyme Q10 Form II crystal having high oxidation stability or a crystalline solid thereof.

Example aspects of the present embodiment are described as follows.

(1) A method for producing a reduced coenzyme Q10 Form II crystal or a crystalline solid thereof, the method using a crystallizer provided with a crystallization unit, a turbidity detection unit capable of detecting a turbidity in the crystallization unit, and a temperature adjustment unit capable of adjusting a temperature in the crystallization unit, and the method comprising:

accommodating a mixed solution containing an alcohol and a reduced coenzyme Q10 in the crystallization unit;

adding a reduced coenzyme Q10 Form II crystal as a seed crystal to the mixed solution; and precipitating a reduced coenzyme Q10 Form II crystal in the mixed solution after adding the seed crystal, wherein the precipitation includes controlling a temperature with the temperature adjustment unit based on a turbidity change rate obtained by the turbidity detection unit.

(2) The method according to (1), wherein the control is to vary at least one of a temperature and a cooling rate of the mixed solution based on a predetermined range and a measurement value of the turbidity change rate.

(3) The method according to (2), wherein the predetermined range is a range determined based on a change rate of formazan turbidity (FTU), and the predetermined range is set within a range of 2 to 45 FTU/min in a period during which FTU shifts from 1,000 to 10,000.

(4) The method according to any one of (1) to (3), wherein the alcohol is a monohydric alcohol having 1 to 5 carbon atoms.

(5) The method according to (4), wherein the monohydric alcohol having 1 to 5 carbon atoms is ethanol.

(6) The method according to any one of (1) to (5), wherein the alcohol is an alcohol of 95% or more by weight based on a total amount of water and alcohol.

(7) A crystallizer for a reduced coenzyme Q10 Form II crystal, comprising:

a crystallization unit capable of accommodating a mixed solution containing an alcohol and a reduced coenzyme Q10;

a turbidity detection unit for detecting a turbidity change rate of the mixed solution accommodated in the crystallization unit;

a temperature adjustment unit capable of adjusting a temperature inside the crystallization unit; and a control unit for controlling the adjustment of the temperature by the temperature adjustment unit based on the turbidity change rate of the mixed solution obtained by the turbidity detection unit.

(8) The crystallizer according to (7), wherein the control is to vary at least one of a temperature and a cooling rate of the mixed solution based on a predetermined range and a measurement value of the turbidity change rate.

(9) The crystallizer according to (8), wherein the predetermined range is a range determined based on a change rate of formazan turbidity (FTU), and the predetermined range is set within a range of 2 to 45 FTU/min in a period during which FTU shifts from 1,000 to 10,000.

The present description encompasses the specification and/or drawings in JP Patent Application No. 2021-053784 which serves as the basis of the priority of the present application.

Advantageous Effects of Invention

A reduced coenzyme Q10 Form II crystal or a crystalline solid thereof can be stably produced according to the method for producing a reduced coenzyme Q10 Form II crystal or a crystalline solid thereof of the present disclosure. In addition, the crystallizer of the present disclosure can be used when carrying out the production method.

BRIEF DESCRIPTION OF DRAWING

FIG. 1 is a schematic diagram of one aspect of the crystallizer of the present embodiment.

DESCRIPTION OF EMBODIMENTS

Hereinafter, the present invention will be described in detail.

<Reduced Coenzyme Q10>

The "reduced coenzyme Q10" herein may partially include oxidized coenzyme Q10, if it includes reduced coenzyme Q10 as a main component. The "main component" herein means that it is included in a proportion of, for example, 50% by weight or more, usually 60% by weight or more, preferably 70% by weight or more, more preferably 80% by weight or more, further preferably 90% by weight or more, particularly preferably 95% by weight or more, and further particularly preferably 98% by weight or more. Herein, the above-described percentage is the percentage of the reduced coenzyme Q10 to the total weight of coenzyme Q10.

Besides, as mentioned above, the reduced coenzyme Q10 includes two forms of crystal polymorphisms, namely, the conventionally known Form I and a recently newly found Form II. Specifically, the crystal form of reduced coenzyme Q10 having a melting point around 48° C. and showing characteristic peaks at diffraction angles (2θ±0.2°) of 3.1°, 18.7°, 19.0°, 20.2° and 23.0° in powder X-ray (Cu-Kα) analysis is Form I, whereas the crystal form of reduced coenzyme Q10 having a melting point around 52° C. and showing characteristic peaks at diffraction angles (2θ±0.2°) of 11.5°, 18.2°, 19.3°, 22.3°, 23.0° and 33.3° in powder X-ray (Cu-Kα) analysis is Form II. In the present description, the crystal of reduced coenzyme Q10 that satisfies at least one of the following conditions is referred to as a "reduced coenzyme Q10 Form II crystal": when the temperature is increased at a rate of 5° C./min by differential scanning calorimetry (DSC), the reduced coenzyme Q10 crystal has an endothermic peak at 54±2° C.; when the same measurement is carried out at a temperature rising rate of 1° C./min, the reduced coenzyme Q10 crystal has an endothermic peak at 52±2° C.; and in powder X-ray (Cu-Kα) analysis, the reduced coenzyme Q10 crystal shows characteristic peaks at diffraction angles (2θ±0.2°) of 11.5°, 18.2°, 19.3°, 22.3°, 23.0° and 33.3°. Of course, the reduced coenzyme Q10 crystal may satisfy all of said three conditions.

Moreover, the term "crystalline solid" is used in the present description to mean a solid containing therein a portion having a crystal structure and an amorphous portion having no crystal structure. In other words, the "crystalline solid thereof" in the expression "reduced coenzyme Q10 Form II crystal or a crystalline solid thereof" means a "solid containing therein a portion having a crystalline structure of reduced coenzyme Q10 Form II crystal and an amorphous component having no crystalline structure."

<Alcohol>

The present inventors found that the saturation concentration of a Form II crystal is lower than the saturation concentration of a Form I crystal in an alcohol, which makes it possible to efficiently precipitate a reduced coenzyme Q10 Form II crystal using an alcohol as a solvent for reduced coenzyme Q10.

The alcohol is preferably a monohydric alcohol having 1 to 5 carbon atoms. Examples of a monohydric alcohol having 1 to 5 carbon atoms include methanol, ethanol, n-propanol, isopropanol, n-butanol, isobutanol, and n-pentanol. As the alcohol, ethanol is particularly preferable because the saturation concentration of Form II crystal is sufficiently lower than the saturation concentration of Form I crystal and is easy to handle. As the alcohol, those exemplified above may be used alone, or two or more thereof may be mixed and used.

The alcohol used in the present description may be a solvent containing alcohol as a main component, and may be a hydrous alcohol containing water. As for the alcohol, the lower the water content, the easier the selective precipitation of Form II crystals. Therefore, the alcohol concentration with respect to the total amount of water and alcohol is, for example, 80% by weight or more, usually 90% by weight or more, preferably 95% by weight or more, more preferably 97% by weight or more, further preferably 99% by weight or more, and particularly preferably 99.5% by weight or more. An alcohol having an alcohol concentration of 99.5% by weight or more means anhydrous alcohol. In addition, the upper limit of the alcohol concentration is 100% by weight or less.

Particularly preferable alcohols are hydrous ethanol and anhydrous ethanol. The ethanol concentration with respect to the total amount of water and ethanol is, for example, 80% by weight or more, usually 90% by weight or more, preferably 95% by weight or more, more preferably 97% by weight or more, further preferably 99% by weight or more, and particularly preferably 99.5% by weight or more. In addition, the upper limit of the ethanol concentration is 100% by weight or less.

<Method for Producing Reduced Coenzyme Q10 Form II Crystal or Crystalline Solid Thereof>

The method for producing a reduced coenzyme Q10 Form II crystal or a crystalline solid thereof according to the present embodiment is a method for producing a reduced coenzyme Q10 Form II crystal or a crystalline solid thereof, the method using a crystallizer provided with a crystallization unit, a turbidity detection unit capable of detecting a turbidity in the crystallization unit, and a temperature adjustment unit capable of adjusting a temperature in the crystallization unit, and the method including: accommodating a mixed solution containing an alcohol and a reduced coenzyme Q10 in the crystallization unit; adding a reduced coenzyme Q10 Form II crystal as a seed crystal to the mixed solution; and precipitating a reduced coenzyme Q10 Form II crystal in the mixed solution after adding the seed crystal, wherein the precipitation includes controlling a temperature with the temperature adjustment unit based on a turbidity change rate obtained by the turbidity detection unit.

The step of adding a reduced coenzyme Q10 Form II crystal as a seed crystal may be referred to as "seed crystal addition step" and the step of precipitating a reduced coenzyme Q10 Form II crystal may be referred to as "crystal precipitation step" in the following description.

The method for producing a reduced coenzyme Q10 Form II crystal according to the present embodiment uses a crystallizer provided with a crystallization unit, a turbidity detection unit capable of detecting a turbidity in the crystallization unit, and a temperature adjustment unit capable of adjusting a temperature in the crystallization unit. FIG. 1 shows a schematic diagram of one aspect of the crystallizer. In the crystallizer shown in FIG. 1, a state in which a mixed solution 3 containing alcohol and reduced coenzyme Q10 is accommodated inside a crystallization unit 1 is illustrated. The crystallization unit 1 is provided with a turbidity detection unit 5 (e.g., a turbidimeter) and preferably a temperature detector 7 (e.g., a thermometer). In the crystallizer shown in FIG. 1, the temperature of the crystallization unit 1 can be adjusted by a temperature adjustment unit composed of a constant temperature water bath 9 and a heating medium 11 (e.g., water). In the crystallizer shown in FIG. 1, the turbidity detection unit 5 has a turbidity sensor **5*a* and a converter 5*b* that converts the signal detected by the turbidity sensor 5*a* into turbidity, such as an FTU value. The crystallizer also has a control unit 13 for controlling the adjustment of the temperature by the temperature adjustment unit based on the turbidity change of the mixed solution obtained by the turbidity detection unit 5. It is preferable that the crystallizer shown in FIG. 1 further has a stirring blade 15 for stirring the inside of the crystallization unit 1. The crystallizer shown in FIG. 1** is one aspect of the crystallizer for a reduced coenzyme Q10 Form II crystal according to the present embodiment, which will be described later.

The control unit 13 is a control mechanism that controls temperature adjustment by the temperature adjustment unit and may be a central control mechanism that controls other conditions (e.g., stirring conditions). The control unit 13 can be composed of, for example, a software program for realizing various processes, a CPU that executes the software program, different hardware controlled by the CPU, and the like. In one aspect, the control unit 13 is a computer, including a CPU, an input/output circuit, and the like. Programs, data, and control parameters required to operate the control unit 13 can be stored in a storage unit (not shown) in the present embodiment. Note that the storage destination of these programs and data is not particularly limited. These programs, data, and the like may be stored in a separately provided storage device such as a disk or flash memory. Alternatively, the information may be stored in a communicatively connected external server, storage unit, or the like.

A mixed solution containing alcohol and reduced coenzyme Q10 accommodated in the crystallization unit is not particularly limited as long as it contains alcohol and reduced coenzyme Q10. It may be a solution in which reduced coenzyme Q10 is homogeneously dissolved in alcohol or a slurry in which reduced coenzyme Q10 is partially dissolved but partially not dissolved and suspended in alcohol. Preferably, it is a solution in which reduced coenzyme Q10 is homogeneously dissolved in alcohol.

Reduced coenzyme Q10 used in a mixed solution containing alcohol and reduced coenzyme Q10 may be either a crystalline or amorphous state, and the crystal polymorphism thereof is not limited. Accordingly, a conventionally known reduced coenzyme Q10 Form I can also be used. In addition, since the purity of reduced coenzyme Q10 can be increased in crystal precipitation, reduced coenzyme Q10 having impurities, or unpurified or roughly purified reduced coenzyme Q10 may also be used. Furthermore, an extract of reduced coenzyme Q10 obtained by a conventionally known method, or a reaction solution containing reduced coenzyme Q10 obtained from oxidized coenzyme Q10 by a known reduction method may also be used as the mixed solution, directly, or after purification and/or solvent substitution, as necessary.

The mixed solution containing alcohol and reduced coenzyme Q10 may further include an organic solvent other than alcohol (including hydrous alcohol). The content of alcohol (alcohol purity) in the total amount of solvent components is preferably 95% by weight or more, 97% by weight or more, or 99% by weight or more. The upper limit thereof is preferably 100% by weight or less. The alcohol purity is most preferably 99.5% by weight or more. Examples of other organic solvents may include at least one selected from the group consisting of a hydrocarbon, an aliphatic acid ester, and a nitrogen compound.

The concentration of dissolved reduced coenzyme Q10 before seed crystal addition in the mixed solution containing alcohol and reduced coenzyme Q10 is, for example, 2% by weight or more, preferably 3% by weight or more, more preferably 5% by weight or more, further preferably 7% by weight or more, and particularly preferably 9% by weight or more. The concentration of dissolved reduced coenzyme Q10 before seed crystal addition is, for example, 50% by weight or less, preferably 45% by weight or less, more preferably 30% by weight or less, further preferably 20% by weight or less, and particularly preferably 15% by weight or less.

A mixed solution containing alcohol and reduced coenzyme Q10 can be obtained by heating a raw material mixture containing alcohol and reduced coenzyme Q10 to a temperature of, for example, 42° C. or higher to dissolve reduced coenzyme Q10. The temperature is preferably 70° C. or lower, more preferably 55° C. or lower. Before adding a seed crystal after dissolving reduced coenzyme Q10, it is preferable to cool the mixed solution containing alcohol and reduced coenzyme Q10 to a temperature when adding a seed crystal, as described later.

The added amount of the reduced coenzyme Q10 Form II crystal serving as a seed crystal (the added amount of seed crystal) is not particularly limited. The added amount of the reduced coenzyme Q10 Form II crystal serving as a seed crystal is preferably 0.1% by weight or more, more preferably 0.5% by weight or more, further preferably 0.8% by weight or more, and particularly preferably 1% by weight or more, based on the amount of the reduced coenzyme Q10 in the mixed solution before seed crystal addition (100% by weight). The upper limit thereof is not particularly limited, but is preferably 20% by weight or less, more preferably 4% by weight or less, and further preferably 2.2% by weight or less, based on the amount of the reduced coenzyme Q10 in the mixed solution before seed crystal addition (100% by weight). Besides, the reduced coenzyme Q10 crystal used as a seed crystal may also comprise reduced a coenzyme Q10 Form I crystal or an amorphous solid, as long as the reduced coenzyme Q10 crystal comprises a reduced coenzyme Q10 Form II crystal. However, the higher the purity of reduced coenzyme Q10 Form II crystal, the more preferable. Thus, it may be preferable to use, as a seed crystal, a reduced coenzyme Q10 crystal comprising, for example, 50% by weight or more of, preferably 75% by weight or more of, more preferably 80% by weight or more of, and further preferably 90% by weight or more of reduced coenzyme Q10 Form II crystal.

The temperature of the mixed solution when adding a seed crystal is preferably 30° C. to 43° C. The temperature of the mixed solution when adding a seed crystal is more preferably 32° C. or higher, particularly preferably 34° C. or higher, and further preferably 40° C. or less. Selective precipitation of reduced coenzyme Q10 Form II crystal is easy in this range.

The crystal precipitation step includes controlling a temperature with the temperature adjustment unit based on a turbidity change rate obtained by the turbidity detection unit. In the crystal precipitation step, an increase in turbidity means crystal precipitation, and the turbidity change rate (the amount of change in turbidity per unit time) is an index of the crystal precipitation rate. It can be said that the control is to vary at least one of a temperature and a cooling rate of the mixed solution based on a predetermined range and a measurement value of the turbidity change rate. For example, in a case in which the measured turbidity change rate is greater than a predetermined range, it can be determined that the crystal precipitation rate is high, and the temperature of the mixed solution can be increased, or the cooling rate can be decreased. In another example, in a case in which the measured turbidity change rate is smaller than a predetermined range, it can be determined that the crystal precipitation rate is low, and the temperature of the mixed solution can be decreased, or the cooling rate can be increased. The control is preferably performed based on a predetermined range of the turbidity change rate and a measurement value of the turbidity change rate. However, it is not necessary to always perform the control to change at least one of the temperature and the cooling rate of the mixed solution in a case in which the measurement value deviates from the predetermined range. In a case in which the measurement value of the turbidity change rate is expected to return within the predetermined range quickly, the temperature and the cooling rate of the mixed solution do not need to be changed. For example, in a case in which the temperature of the mixed solution is maintained constant, as the crystal precipitation progresses, the crystal precipitation rate slows down and the turbidity change rate decreases. Therefore, for example, even when the turbidity change rate temporarily exceeds the predetermined range, it is not necessary to change the temperature and the cooling rate of the mixed solution in a case in which the turbidity change rate may fall quickly within the predetermined range. In addition, the control may be performed by changing at least one of the temperature and the cooling rate of the mixed solution each time based on the turbidity change rate. Alternatively, the control may be performed by setting a temperature program in advance and changing at least one of the temperature and the cooling rate of the mixed solution when an abnormality occurs in the turbidity change rate.

The turbidity may be based on any index, such as kaolin turbidity or formazan turbidity (FTU), and from the viewpoint of versatility, formazan turbidity is preferable.

The turbidity change rate can be calculated by, for example, dividing the difference between the turbidity at a certain time point and the turbidity measured before that time point by the measurement interval.

For example, the turbidity change rate at a certain time point (T) can be calculated by the following formula:

$$\text{Turbidity change rate}_T(\text{Turbidity/min})=(\text{Turbidity measurement value}_T-\text{Turbidity measurement value}_{T-X})/X(\text{min})$$

(in the formula, the turbidity change rate T means a turbidity change rate at a time point (T), the turbidity measurement value$_T$ means a turbidity measurement value at a time point (T), and the turbidity measurement value TA means a turbidity measurement value X minutes before the time point (T)).

In a case in which the turbidity to be measured is formazan turbidity (FTU), the change rate of formazan turbidity (FTU) at a certain time point (T) can be calculated by the following formula:

$$\text{Change rate of formazan turbidity}_T(\text{FTU/min})=(\text{Turbidity measurement value}_T(\text{FTU})-\text{Turbidity measurement value}_{T-X}(\text{FTU}))/X(\text{min})$$

(in the formula, the change rate of formazan turbidity$_T$ means a change rate of formazan turbidity (FTU) at a time point (T), the turbidity measurement value$_T$ (FTU) means a measurement value of formazan turbidity (FTU) at a time point (T), and the turbidity measurement value$_{T-X}$ (FTU) means a measurement value of formazan turbidity (FTU) X minutes before the time point (T)).

The frequency of obtaining the turbidity change rate is not particularly limited. However, in the case of excessively frequent measurement of the turbidity change rate, the turbidity change rate may be unstable due to measurement errors, concentration differences in the mixed solution, and the like. In the case of excessively infrequent measurement of the turbidity change rate, the crystal precipitation rate may be insufficiently controlled. From such viewpoints, the turbidity change rate is preferably determined, for example, every 3 to 180 minutes, more preferably every 5 to 30 minutes, and further preferably every 10 to 30 minutes. Note that the measurement interval may or may not be constant, and is not particularly limited.

In a case in which the turbidity to be measured is formazan turbidity (FTU) and the turbidity change rate is within a range determined based on the change rate of formazan turbidity (FTU), the predetermined range is set within a range of 2 to 45 FTU/min in a period during which the formazan turbidity (FTU) shifts from 1,000 to 10,000 in one preferred aspect. The predetermined range is more preferably set within a range of 2 to 43 FTU/min and further preferably set within a range of 2 to 35 FTU/min in a period during which the formazan turbidity (FTU) shifts from 1,000 to 10,000. Turbidity such as formazan turbidity (FTU) increases as crystal precipitation progresses. In particular, immediately after addition of the seed crystal, the formazan turbidity (FTU) tends to increase rapidly, and measurement errors tend to increase. Therefore, it is only sometimes realistic to maintain a constant change rate of formazan turbidity (FTU) from the time of seed crystal addition. In the above-described aspect, the predetermined range is set in a period during which the formazan turbidity (FTU) shifts from 1,000 to 10,000. By setting such a predetermined range, it is possible to perform a method for producing a reduced coenzyme Q10 Form II crystal or a crystalline solid thereof with good reproducibility.

It is preferable that the mixed solution is a solution in which reduced coenzyme Q10 is homogeneously dissolved in alcohol when adding a seed crystal. In a case in which the turbidity to be measured is formazan turbidity (FTU), the formazan turbidity (FTU) of the mixed solution when adding a seed crystal is usually 0 to 250, preferably 0 to 230, and more preferably 0 to 200. This range is preferable because reduced coenzyme Q10 Form II crystals are preferentially precipitate.

In a case in which the turbidity to be measured is formazan turbidity (FTU), the temperature of the mixed solution in the period during which the formazan turbidity (FTU) shifts from 1,000 to 10,000 is preferably 30° C. to 43° C., more preferably 30.5° C. to 42° C., and particularly preferably 31° C. to 41° C. This range of the temperature of the mixed solution is preferable because it is easy to maintain change rate of formazan turbidity (FTU) within the above-described range.

In a case in which the turbidity to be measured is formazan turbidity (FTU), the temperature of the mixed solution at 10,000 FTU is preferably 29° C. to 38° C., more preferably 30° C. to 37° C., and particularly preferably 31° C. to 36° C.

In the crystal precipitation step, the temperature of the mixed solution may be constant but may be lowered stepwise or continuously. In addition, the temperature of the mixed solution may be maintained at a constant temperature for a certain period and then lowered stepwise or continuously. In one preferred aspect, the temperature of the mixed solution when adding a seed crystal is 34° C. to 38° C. and the temperature of the mixed solution at 10,000 FTU is 30° C. to 37° C. It is preferable that the temperature at 10,000 FTU is lower by 0.4° C. to 8° C. than the temperature when adding a seed crystal. Maintaining a constant temperature means preferably maintaining a predetermined temperature (set temperature)±3° C. and more preferably maintaining a predetermined temperature (set temperature)±1° C.

The cooling rate for reducing the temperature of the mixed solution is preferably 0.05° C./hr to 20° C./hr and more preferably 0.1° C./hr to 15° C./hr. In a preferred aspect, the cooling rate may be changed over time. For instance, an aspect in which the temperature is maintained for a certain period, e.g., 0.5 to 8 hours after seed crystal addition, following which the cooling rate is set to 0.05° C./hr to less than 0.5° C./hr for 3 to 20 hours, and then 0.5° C./hr to 15° C./hr and an aspect in which after seed crystal addition, the cooling rate is set to 0.05° C./hr to less than 0.5° C./hr for 3 to 20 hours, and then 0.5° C./hr to 15° C./hr can be mentioned.

It is preferable to lower the temperature of the mixed solution also after the formazan turbidity (FTU) reaches 10,000 FTU as the upper limit for measurement for crystal precipitation in the crystal precipitation step in a case in which the turbidity to be measured is formazan turbidity (FTU). The cooling rate at that time can be set, for example, based on the range described above. When the temperature of the mixed solution reaches 23° C. to 34° C., most of the reduced coenzyme Q10 contained in the mixed solution has been precipitated. Therefore, it is also possible to increase the cooling rate to a range of 1° C./hr to 20° C./hr after the temperature reaches 23° C. to 34° C., for example.

The temperature at which the crystal precipitation step ends, namely the end point temperature, is preferably 25° C. or lower, more preferably 20° C. or lower, still more preferably 10° C. or lower, yet still more preferably 7° C. or lower, and even still more preferably 5° C. or lower. The lower limit of the end point temperature is the solidification temperature of the mixed solution system, which is preferably 0° C. or higher.

Crystal precipitation is preferably carried out, while forced-flowing the mixed solution. From the viewpoint of suppressing the formation of supersaturation and smoothly conducting nucleation and/or crystal growth, or from the viewpoint of the achievement of high quality, flowing may be given to the mixed solution at a power required for stirring per unit volume of generally 0.003 kW/m$^3$ or more, preferably 0.004 kW/m$^3$ or more, more preferably 0.005 kW/m$^3$ or more, and further preferably 0.006 kW/m$^3$ or more. In addition, flowing may be given to the mixed solution at a power required for stirring of generally 0.1 kW/m$^3$ or less and preferably 0.03 kW/m$^3$ or less. The forced-flowing is generally given by the rotation of a stirring blade. However, if the above-described flowing is obtained, the use of the stirring blade is not always necessary, and for example, a method involving circulation of the mixed solution or the like may be utilized.

The reduced coenzyme Q10 Form II crystal obtained by the above method is recovered through a step of solid-liquid separation and drying by a conventionally known method described in, for example, Patent Literature 2 or 3. For example, pressure filtration or centrifugal filtration can be used for solid-liquid separation. In addition, the crystal or crystalline solid after drying can also be recovered by pulverization or classification (sieving), if necessary.

In the present embodiment, as one of more preferred aspects, after completion of the aforementioned solid-liquid separation, the reduced coenzyme Q10 Form II crystal is dried with warming, so that the content rate of the reduced coenzyme Q10 Form II crystal can be improved. For this purpose, the drying temperature is preferably 46° C. or higher, more preferably 47° C. or higher, and further preferably 49° C. or higher. The upper limit of the drying temperature is generally 52° C. or lower, and preferably 51° C. or lower. When the drying temperature is lower than 46° C., drying progresses, but the content rate of the reduced coenzyme Q10 Form II crystal is hardly improved. On the other hand, when the drying temperature exceeds 52° C., there may be a case where the reduced coenzyme Q10 crystal is melted during the drying.

Besides, when the desired content rate of the reduced coenzyme Q10 Form II crystal has already been achieved in the crystal precipitation step, the aforementioned drying conditions may not apply, and the drying may be carried out at a temperature of, for example, 25° C. or higher, preferably 30° C. or higher, and more preferably 35° C. or higher.

In addition, the warming time in the case of performing drying is not particularly limited, but it is preferably 4 hours or more, more preferably 10 hours or more, and further preferably 20 hours or more. The upper limit of the warming time is not particularly limited, but it is usually 72 hours or less, preferably 48 hours or less, and more preferably 36 hours or less.

Besides, individual steps in the method of the present embodiment, specifically, the above-described step of accommodating a mixed solution in the crystallization unit, seed crystal addition step, crystal precipitation step, recovery step such as solid-liquid separation or drying, and other treatment steps are preferably performed under a deoxygenated atmosphere. The deoxygenated atmosphere can be achieved by the replacement of the atmosphere with an inert gas, reduction of the pressure, boiling, or a combination thereof. The replacement of the atmosphere with an inert gas, namely, an inert gas atmosphere is preferably used. Examples of the inert gas include nitrogen gas, helium gas, argon gas, hydrogen gas, and carbon dioxide, and preferably nitrogen gas.

Whether or not the reduced coenzyme Q10 Form II crystal is contained in the obtained reduced coenzyme Q10 crystal or a crystalline solid thereof, and the content rate thereof can be determined by measuring with, for example, a differential scanning calorimeter (DSC).

As mentioned above, when the reduced coenzyme Q10 Form II crystal is measured with DSC at a temperature rising rate of 1C/min, it exhibits an endothermic peak around 52±2° C. On the other hand, the reduced coenzyme Q10 Form I crystal exhibits an endothermic peak around 48±1° C. under the same conditions as those described above. Even in a state in which the reduced coenzyme Q10 Form II crystal is mixed with the conventional reduced coenzyme Q10 Form I crystal or a crystalline solid thereof, the presence or absence of the reduced coenzyme Q10 Form II crystal or the content rate thereof can be determined based on the presence or absence of the above-described peak around 52±2° C., the height of the endothermic peak, or the ratio of the endothermic amount. According to the present invention, a high-purity reduced coenzyme Q10 Form II crystal or a crystalline solid thereof can be efficiently obtained. According to the present embodiment, a reduced coenzyme Q10 Form II crystal can be obtained by the crystal precipitation step. A crystalline solid may be obtained by partially melting the crystal by the subsequent drying step or the like. Therefore, the present embodiment also encompasses a case in which a crystal is obtained and a case in which a crystalline solid is obtained.

<Crystallizer for Reduced Coenzyme Q10 Form II Crystal>

The crystallizer for a reduced coenzyme Q10 Form II crystal according to the present embodiment is a crystallizer for a reduced coenzyme Q10 Form II crystal comprising: a crystallization unit capable of accommodating a mixed solution containing an alcohol and a reduced coenzyme Q10; a turbidity detection unit for detecting a turbidity change rate of the mixed solution accommodated in the crystallization unit; a temperature adjustment unit capable of adjusting a temperature inside the crystallization unit; and a control unit for controlling the adjustment of the temperature by the temperature adjustment unit based on the turbidity change rate of the mixed solution obtained by the turbidity detection unit.

The crystallizer according to the present embodiment is an apparatus capable of carrying out the above-described method for producing a reduced coenzyme Q10 Form II crystal or a crystalline solid thereof.

As a schematic diagram showing one aspect of the crystallizer according to the present embodiment, the crystallizer shown in FIG. 1 can be mentioned. A turbidity sensor 5*a* is installed in the crystallization unit 1, and more specifically, the turbidity sensor 5*a* is installed inside the crystallization unit 1 in FIG. 1. As another aspect, a light-transmitting material such as glass may be used for all or part of the crystallization unit, and the turbidity sensor 5*a* may be installed outside the crystallization unit. In FIG. 1, the temperature adjustment unit is disposed outside the crystallization unit 1 as the constant temperature water bath 9 and the heating medium 11, but in another aspect, it may be installed inside the crystallization unit 1. For example, the temperature adjustment unit may be provided by installing a heater or the like inside the crystallization unit 1.

It is preferable that the control performed in the control unit is to vary at least one of a temperature and a cooling rate of the mixed solution based on a predetermined range and a measurement value of the turbidity change rate. For example, in the control unit, it is preferable to implement software for executing a program stored in the storage unit to compare the measurement value of the turbidity change rate with the predetermined range of the turbidity change rate stored in the storage unit to determine the necessity of changing at least one of the temperature and the cooling rate of the mixed solution and activate the temperature adjustment unit in response to the result to control the temperature. In the case of the formazan turbidity (FTU), the predetermined range of the turbidity change rate is within a range determined based on the change rate of formazan turbidity (FTU), and the predetermined range is set within a range of 2 to 45 FTU/min in a period during which the formazan turbidity (FTU) shifts from 1,000 to 10,000 in one preferred aspect. The predetermined range is more preferably set within a range of 2 to 43 FTU/min and further preferably set within a range of 2 to 35 FTU/min in a period during which the formazan turbidity (FTU) shifts from 1,000 to 10,000.

EXAMPLES

Hereinafter, the present embodiment will be described with reference to Examples. However, the present disclosure is not limited by these Examples.

<Percentage of Form II Crystal in Reduced Coenzyme Q10 Crystal>

The reduced coenzyme Q10 crystals obtained in Examples were analyzed by DSC measurement under the following conditions. From the height (Difference Y) of the endothermic peak of the obtained reduced coenzyme Q10 Form I crystal (hereinafter referred to as "Difference Form I-Y") and the height (Difference Y) of the endothermic peak of the obtained reduced coenzyme Q10 Form II crystal obtained (hereinafter referred to as "Difference Form II-Y," the percentage of the reduced coenzyme Q10 Form II crystal in each reduced coenzyme Q10 crystal was calculated based on the following formula:

$$\text{Form II percentage (\%)}=\text{Difference Form II-}Y/(\text{Difference Form I-}Y+\text{Difference Form II-}Y)\times 100$$

(DSC Measurement Conditions)

Apparatus: DSC 6220 (manufactured by SII Nano Technology Inc.)

Sample container: Aluminum pan & cover (SSC000C008)

Rate of temperature rise: 1° C./min

Amount of sample: 5±2 mg

<Method for Determining Change Rate of Formazan Turbidity (FTU)>

For the change rate of formazan turbidity (FTU) in Examples, the formazan turbidity (FTU) of a mixed solution containing ethanol and reduced coenzyme Q10 was measured with a turbidimeter. The change rate of formazan turbidity (FTU) at a certain time point (T) was calculated by the following formula. In addition, the turbidimeter used in the present embodiment was calibrated to give a turbidity (FTU) of 9,999 FTU when a reduced coenzyme Q10 crystal was present in the mixed solution at a concentration of 40000 mg/L:

$$\text{Change rate of formazan turbidity}_T\text{(FTU/min)}=(\text{Turbidity measurement value}_T\text{(FTU)}-\text{Turbidity measurement value}_{T\text{-}X}\text{(FTU)})/X\text{(min)}$$

(in the formula, the change rate of formazan turbidity$_T$ means a change rate of formazan turbidity (FTU) at a time point (T), the turbidity measurement value$_T$ (FTU) means a measurement value of formazan turbidity (FTU) at a time point (T), and the turbidity measurement value$_{T-X}$ (FTU) means a measurement value of formazan turbidity (FTU) X minutes before the time point (T)). Turbidimeter: Backscattered light turbidity sensor (InPro8200, METTLER TOLEDO) Measurement range: 0 to 10,000 FTU Turbidity (FTU) measurement was carried out immediately after seed crystal addition until the turbidity reached 10,000 FTU as the upper limit for measurement. The change rate of formazan turbidity (FTU) was calculated. As shown in the above formula, the change rate of formazan turbidity (FTU) at a certain time point T was obtained by calculating the increase in the turbidity (FTU) at the time point T from the turbidity (FTU) at the time point X minutes before (T-X min) and dividing the increase by X (min). In Examples, the change rate of formazan turbidity (FTU) was calculated from the measured formazan turbidity (FTU), the previously measured formazan turbidity (FTU), and the measurement interval.

<Method for Evaluating Oxidation Stability (Relative Percentage of QH)>

The oxidation stability of the reduced coenzyme Q10 crystals obtained in Examples was evaluated by the following method.

The reduced coenzyme Q10 crystals obtained in Examples were stored in an open system for one month in a constant temperature bath set at 40° C. and RH (relative humidity) of 75% and at 25° C. and RH of 60% and then subjected to high-performance liquid chromatography to calculate the content ratio of reduced coenzyme Q10 (QH) and oxidized coenzyme Q10.

The oxidation stability of reduced coenzyme Q10 crystal was calculated as a relative percentage of QH by the following formula based on the relative value with the content of reduced coenzyme Q10 for the initial reduced coenzyme Q10 crystal before storage in a constant temperature bath, i.e., the content of reduced coenzyme Q10 when measured using the crystals obtained in Examples immediately after obtaining the crystals, as 100.

$$\text{Relative percentage of }QH\text{ (\%)}=\text{Content of reduced coenzyme }Q10\text{ after storage/Content of initial reduced coenzyme }Q10\times 100$$

Conditions for the high performance liquid chromatography, by which the reduced coenzyme Q10 concentration and the oxidized coenzyme Q10 concentration were measured, are shown below.

(HPLC Conditions)

Column: SYMMETRY C18 (manufactured by Waters); 250 mm (length), 4.6 mm (inner diameter)

Mobile phase: $C_2H_5OH$:$CH_3OH$=4:3 (v:v)

Detection wavelength: 210 nm

Flow rate: 1 ml/min

Example 1

The inside of a separable flask with a volume of 3 L was replaced with nitrogen, and 160 g of reduced coenzyme Q10 and 1440 g of ethanol having a purity of 99.5% by weight or more were then charged thereto (reduced coenzyme Q10 concentration: 10 wt %). Thereafter, the obtained mixture was warmed to 50° C. while stirring with a stirring blade (power required for stirring: 0.03 kw/m$^3$) to obtain a homogeneous reduced coenzyme Q10 solution (QH solution) (1600 g, 2800 mL).

The QH solution at 50° C. was cooled to 36.0° C. while stirring with a stirring blade (power required for stirring: 0.03 kw/m$^3$). To the QH solution cooled to 36.0° C. (FTU: 18), 3.2 g (2.0 wt %) of a reduced coenzyme Q10 Form II crystal was added as a seed crystal to initiate the precipitation of reduced coenzyme Q10 crystal (crystallization). Hereinafter, the QH solution to which a seed crystal was added is referred to as "mixed solution for crystallization."

After seed crystal addition, the formazan turbidity in the mixed solution was measured regularly until the formazan turbidity (FTU) in the mixed solution reached 10,000. The cooling rate and the cooling temperature were controlled such that the change rate of formazan turbidity (FTU) was around 20.8 FTU/min until the formazan turbidity (FTU) shifted from 1,000 to 10,000. Once the formazan turbidity in the mixed solution reached 10,000 FTU, the temperature was cooled to 25° C. at 1° C./hr and then from 25° C. to 1° C. at 10° C./hr.

The slurry was cooled to 1° C. and then subjected to solid-liquid separation by filtration, and the resulting crystal was dried under reduced pressure at 40° C. for 24 hours to obtain a reduced coenzyme Q10 Form II crystal.

The percentage of Form II crystal in the obtained reduced coenzyme Q10 crystal was 100%, and thus no reduced coenzyme Q10 Form I crystal was contained therein. In addition, the obtained relative percentage of QH for the reduced coenzyme Q10 Form II crystal was 91.8% at 25° C. and RH 60% for 1 month and 88.1% at 40° C. and RH 75% for 1 month.

Table 1 shows the elapsed time, turbidity, set temperature, and change rate of formazan turbidity (FTU) when the formazan turbidity (FTU) of Example 1 reached around 1,000 (942) as 0 min.

TABLE 1

| Elapsed time (min) | Set temperature (° C.) | Turbidity (FTU) | Change rate of formazin turbidity (FTU) (FTU/min) |
|---|---|---|---|
| 0 | 35.4 | 942 | — |
| 20 | 35.0 | 1242 | 15.0 |
| 40 | 34.8 | 1572 | 16.5 |
| 60 | 34.5 | 1859 | 14.4 |
| 80 | 34.5 | 2353 | 24.7 |
| 100 | 34.5 | 2852 | 25.0 |
| 120 | 34.4 | 3333 | 24.0 |
| 140 | 34.4 | 3788 | 22.8 |
| 160 | 34.4 | 4256 | 23.4 |
| 180 | 34.1 | 4700 | 22.2 |
| 200 | 34.4 | 5149 | 22.8 |
| 220 | 34.3 | 5561 | 20.6 |
| 240 | 34.3 | 5935 | 18.7 |
| 260 | 34.5 | 6198 | 13.1 |
| 280 | 34.4 | 6478 | 14.0 |
| 300 | 34.1 | 6684 | 10.3 |
| 320 | 33.9 | 7284 | 30.0 |
| 340 | 33.9 | 7571 | 14.4 |
| 360 | 33.9 | 7852 | 14.0 |
| 380 | 33.6 | 8189 | 16.9 |
| 400 | 33.4 | 8551 | 18.1 |
| 420 | 33.2 | 8863 | 15.6 |
| 440 | 33.0 | 9319 | 22.8 |
| 460 | 33.1 | 9594 | 13.7 |
| 480 | 33.0 | 9911 | 15.9 |
| 500 | 32.9 | 10142 | 11.5 |

Example 2

The inside of a four-necked flask with a volume of 500 mL was replaced with nitrogen, and 32.8 g of reduced coenzyme Q10 and 295.2 g of ethanol having a purity of 99.5% by weight or more were then charged thereto (reduced coenzyme Q10 concentration: 10 wt %). Thereafter, the obtained mixture was warmed to 50° C. while stirring with a stirring blade (power required for stirring: 0.007 kw/m$^3$) to obtain a homogeneous reduced coenzyme Q10 solution (QH solution) (328 g, 410 mL).

The QH solution at 50° C. was cooled to 34.0° C. while stirring with a stirring blade (power required for stirring: 0.007 kw/m$^3$). To the QH solution cooled to 34.0° C., 0.65 g (2.0 wt %) of a reduced coenzyme Q10 Form II crystal was added as a seed crystal to initiate the precipitation of reduced coenzyme Q10 crystal (crystallization).

After seed crystal addition, the formazan turbidity in the mixed solution was measured regularly until the formazan turbidity (FTU) in the mixed solution reached 10,000. The cooling rate and the cooling temperature were controlled such that the change rate of formazan turbidity (FTU) was around 55.6 FTU/min until the formazan turbidity (FTU) shifted from 1,000 to 10,000. In a case in which the formazan turbidity (FTU) change rate in the mixed solution clearly deviated from 55.6 FTU/min during the control, the mixed solution was heated, and the temperature was maintained for a certain period to adjust the crystallization rate (crystal precipitation rate). Once the formazan turbidity in the mixed solution reached 10,000 FTU, the temperature was cooled to 25° C. at 1° C./hr and then from 25° C. to 1° C. at 10° C./hr.

The slurry was cooled to 1° C. and then subjected to solid-liquid separation by filtration, and the resulting crystal was dried under reduced pressure at 40° C. for 24 hours to obtain a reduced coenzyme Q10 Form II crystal.

The obtained relative percentage of QH for the reduced coenzyme Q10 Form II crystal was 85.1% at 25° C. and RH 60% for 1 month and 81.4% at 40° C. and RH 75% for 1 month.

Table 2 shows the elapsed time, turbidity, set temperature, and change rate of formazan turbidity (FTU) when the formazan turbidity (FTU) of Example 2 reached around 1,000 (870) as 0 min.

TABLE 2

| Elapsed time (min) | Turbidity (FTU) | Set temperature (° C.) | Change rate of formazin turbidity (FTU) (FTU/min) |
|---|---|---|---|
| 0 | 870 | 34.0 | — |
| 9 | 1731 | 34.0 | 95.7 |
| 16 | 2594 | 34.0 | 123.3 |
| 21 | 3148 | 34.0 | 110.8 |
| 28 | 3944 | 34.0 | 113.7 |
| 32 | 4324 | 34.0 | 95.0 |
| 43 | 4815 | 34.5 | 44.6 |
| 53 | 5239 | 34.5 | 42.4 |
| 64 | 5594 | 34.5 | 32.3 |
| 73 | 5831 | 34.5 | 26.3 |
| 83 | 6339 | 34.0 | 50.8 |
| 93 | 6806 | 34.0 | 46.7 |
| 105 | 7306 | 34.0 | 41.7 |
| 118 | 7752 | 34.0 | 34.3 |
| 134 | 8370 | 33.5 | 38.6 |
| 149 | 9000 | 33.5 | 42.0 |
| 158 | 9287 | 33.5 | 31.9 |
| 166 | 9537 | 33.0 | 31.3 |

Example 3

The inside of a separable flask with a volume of 500 mL was replaced with nitrogen, and 32.8 g of reduced coenzyme Q10 and 295.2 g of ethanol having a purity of 99.5% by weight or more were then charged thereto (reduced coenzyme Q10 concentration: 10 wt %). Thereafter, the obtained mixture was warmed to 50° C. while stirring with a stirring blade (power required for stirring: 0.007 kw/m$^3$) to obtain a homogeneous reduced coenzyme Q10 solution (QH solution) (328 g, 410 mL).

The QH solution at 50° C. was cooled to 34.5° C. while stirring with a stirring blade (power required for stirring: 0.007 kw/m$^3$). To the QH solution cooled to 34.5° C., 0.65 g (2.0 wt %) of a reduced coenzyme Q10 Form II crystal was added as a seed crystal to initiate the precipitation of reduced coenzyme Q10 crystal (crystallization).

After seed crystal addition, the formazan turbidity in the mixed solution was measured regularly until the formazan turbidity (FTU) in the mixed solution reached 10,000. The cooling rate and the cooling temperature were controlled such that the change rate of formazan turbidity (FTU) was around 33.3 FTU/min until the formazan turbidity (FTU) shifted from 1,000 to 10,000. In a case in which the formazan turbidity (FTU) change rate in the mixed solution clearly deviated from 33.3 FTU/min during the control, the mixed solution was heated, and the temperature was maintained for a certain period to adjust the crystallization rate (crystal precipitation rate). Once the formazan turbidity in the mixed solution reached 10,000 FTU, the temperature was cooled to 25° C. at 1° C./hr and then from 25° C. to 1° C. at 10° C./hr.

The slurry was cooled to 1° C. and then subjected to solid-liquid separation by filtration, and the resulting crystal was dried under reduced pressure at 40° C. for 24 hours to obtain a reduced coenzyme Q10 Form II crystal.

The obtained relative percentage of QH for the reduced coenzyme Q10 Form II crystal was 89.4% at 25° C. and RH 60% for 1 month and 87.3% at 40° C. and RH 75% for 1 month.

Table 3 shows the elapsed time, turbidity, set temperature, and change rate of formazan turbidity (FTU) when the formazan turbidity (FTU) of Example 3 reached around 1,000 (877) as 0 min.

TABLE 3

| Elapsed time (min) | Set temperature (° C.) | Turbidity (FTU) | Change rate of formazin turbidity (FTU) (FTU/min) |
|---|---|---|---|
| 0 | 34.4 | 877 | — |
| 20 | 34.2 | 1675 | 39.9 |
| 40 | 34.4 | 2496 | 41.0 |
| 60 | 34.3 | 3316 | 41.0 |
| 80 | 34.2 | 4045 | 36.4 |
| 100 | 34.1 | 4738 | 34.7 |
| 120 | 33.9 | 5408 | 33.5 |
| 140 | 33.9 | 6241 | 41.6 |
| 160 | 33.9 | 6946 | 35.3 |
| 180 | 33.8 | 7420 | 23.7 |
| 200 | 33.3 | 8021 | 30.1 |
| 220 | 33.5 | 8472 | 22.5 |
| 240 | 33.4 | 8842 | 18.5 |
| 260 | 32.8 | 9396 | 27.7 |
| 280 | 32.9 | 9778 | 19.1 |
| 300 | 33.1 | 10067 | 14.4 |

Example 4

The inside of a separable flask with a volume of 500 mL was replaced with nitrogen, and 27.8 g of reduced coenzyme Q10 and 250.2 g of ethanol having a purity of 99.5% by weight or more were then charged thereto (reduced coenzyme Q10 concentration: 10 wt %). Thereafter, the obtained mixture was warmed to 50° C. while stirring with a stirring blade (power required for stirring: 0.007 kw/m$^3$) to obtain a homogeneous reduced coenzyme Q10 solution (QH solution) (278 g, 347 mL).

The QH solution at 50° C. was cooled to 36.8° C. while stirring with a stirring blade (power required for stirring: 0.007 kw/m$^3$). To the QH solution cooled to 36.8° C. (FTU: 683), 0.56 g (2.0 wt %) of a reduced coenzyme Q10 Form II crystal was added as a seed crystal to initiate the precipitation of reduced coenzyme Q10 crystal (crystallization).

After seed crystal addition, the formazan turbidity in the mixed solution was measured regularly until the formazan turbidity (FTU) in the mixed solution reached 10,000. The cooling rate and the cooling temperature were controlled such that the change rate of formazan turbidity (FTU) was around 6.9 FTU/min until the formazan turbidity (FTU) shifted from 1,000 to 10,000. In a case in which the formazan turbidity (FTU) change rate in the mixed solution clearly deviated from 6.9 FTU/min during the control, the mixed solution was heated, and the temperature was maintained for a certain period to adjust the crystallization rate (crystal precipitation rate). Once the formazan turbidity in the mixed solution reached 10,000 FTU, the temperature was cooled to 25° C. at 1° C./hr and then from 25° C. to 1° C. at 10° C./hr.

The slurry was cooled to 1° C. and then subjected to solid-liquid separation by filtration, and the resulting crystal was dried under reduced pressure at 40° C. for 24 hours to obtain a reduced coenzyme Q10 Form II crystal.

The percentage of form II crystal in the obtained reduced coenzyme Q10 crystal was 100%. In addition, the obtained relative percentage of QH for the reduced coenzyme Q10 Form II crystal was 92.2% at 25° C. and RH 60% for 1 month and 90.1% at 40° C. and RH 75% for 1 month.

Tables 4 and 5 show the elapsed time, turbidity, set temperature, and formazan turbidity (FTU) change rate when the formazan turbidity (FTU) of Example 4 reached around 1,000 (933) as 0 min.

TABLE 4

| Elapsed time (min) | Set temperature (° C.) | Turbidity (FTU) | Change rate of formazin turbidity (FTU) (FTU/min) |
|---|---|---|---|
| 0 | 36.9 | 933 | — |
| 30 | 36.6 | 1014 | 2.7 |
| 60 | 37.1 | 1120 | 3.5 |
| 90 | 37.1 | 1245 | 4.2 |
| 120 | 36.5 | 1439 | 6.5 |
| 150 | 36.7 | 1601 | 5.4 |
| 180 | 37.1 | 1782 | 6.0 |
| 210 | 36.3 | 2019 | 7.9 |
| 240 | 36.8 | 2350 | 11.0 |
| 270 | 35.4 | 2413 | 2.1 |
| 300 | 36.7 | 2581 | 5.6 |
| 330 | 36.7 | 3012 | 14.4 |
| 360 | 36.8 | 3131 | 4.0 |
| 390 | 36.6 | 3393 | 8.7 |
| 420 | 36.6 | 3505 | 3.7 |
| 450 | 37.5 | 3867 | 12.1 |
| 480 | 35.7 | 4067 | 6.7 |
| 510 | 37 | 4423 | 11.9 |
| 540 | 37 | 4623 | 6.7 |
| 570 | 36.5 | 4941 | 10.6 |
| 600 | 36.5 | 5216 | 9.2 |
| 630 | 36.6 | 5353 | 4.6 |

TABLE 5

| Elapsed time (min) | Set temperature (° C.) | Turbidity (FTU) | Change rate of formazin turbidity (FTU) (FTU/min) |
|---|---|---|---|
| 660 | 36.1 | 5634 | 9.4 |
| 690 | 36.5 | 5865 | 7.7 |
| 720 | 37.2 | 6065 | 6.7 |
| 750 | 36.9 | 6308 | 8.1 |
| 780 | 36.5 | 6420 | 3.7 |
| 810 | 36.4 | 6589 | 5.6 |
| 840 | 36.5 | 6814 | 7.5 |
| 870 | 36.5 | 7063 | 8.3 |
| 900 | 36.2 | 7326 | 8.7 |
| 930 | 36.6 | 7476 | 5.0 |
| 960 | 36.2 | 7632 | 5.2 |
| 990 | 36.7 | 7775 | 4.8 |
| 1020 | 36.1 | 8006 | 7.7 |
| 1050 | 36 | 8193 | 6.2 |
| 1080 | 36.7 | 8287 | 3.1 |
| 1110 | 36.8 | 8487 | 6.7 |
| 1140 | 36.5 | 8749 | 8.7 |
| 1170 | 36.5 | 8918 | 5.6 |
| 1200 | 36.4 | 8974 | 1.9 |
| 1230 | 36.4 | 9186 | 7.1 |
| 1260 | 36.6 | 9348 | 5.4 |
| 1290 | 36 | 9492 | 4.8 |
| 1320 | 36.4 | 9667 | 5.8 |
| 1350 | 36.8 | 9792 | 4.2 |
| 1380 | 36.5 | 9985 | 6.5 |

Table 6 shows the percentages of Form II crystals (Form II percentages) and the relative percentages of QH for the reduced coenzyme Q10 crystals obtained in Examples.

TABLE 6

| Example | Relative percentage of QH (40° C., 1M) (%) | Relative percentage of QH (25° C., 1M) (%) |
|---|---|---|
| Example 1 | 88.1 | 91.8 |
| Example 2 | 81.4 | 85.1 |

TABLE 6-continued

| Example | Relative percentage of QH (40° C., 1M) (%) | Relative percentage of QH (25° C., 1M) (%) |
|---|---|---|
| Example 3 | 87.3 | 89.4 |
| Example 4 | 90.1 | 92.2 |

The reduced coenzyme Q10 Form II crystals obtained in Examples are excellent in oxidation stability. It is understood that a reduced coenzyme Q10 Form II crystal or a crystalline solid thereof can be stably produced according to the method for producing a reduced coenzyme Q10 Form II crystal or a crystalline solid thereof in the present embodiment.

All publications, patents and patent applications cited in the present description are incorporated herein by reference in their entirety.

The upper and/or lower limits of the numerical ranges described herein can be combined arbitrarily to define a preferred range. For example, a preferred range can be defined by arbitrarily combining the upper and lower limits of the numerical range, a preferred range can be defined by arbitrarily combining the upper limits of the numerical range, and a preferred range can be defined by arbitrarily combining the lower limits of the numerical range.

It should be understood that throughout the present description, expressions in the singular forms also include the concept of their plural forms unless otherwise specifically stated. Thus, articles in the singular forms (e.g., "a," "an," and "the" in the English language) should be understood to include the concept of their plural forms as well, unless otherwise specifically stated.

Although the embodiment of the present invention has been described in detail above, the specific configuration is not limited to this embodiment, and even when there are design changes within the scope of the present disclosure, they are included in the present disclosure.

REFERENCE SIGNS LIST

1 Crystallization unit
3 Mixed solution
5 Turbidity detection unit
5*a* Turbidity sensor
5*b* Transducer
7 Temperature detector
9 Constant temperature water bath
11 Heating medium
13 Control unit
15 Stirring blade

The invention claimed is:

1. A method for producing a reduced coenzyme Q10 Form II crystal or a crystalline solid thereof, comprising:

providing a crystallizer, wherein the crystallizer comprises a crystallization unit, a turbidity detection unit for detecting a turbidity in the crystallization unit, and a temperature adjustment unit for adjusting a temperature in the crystallization unit;

providing a mixed solution comprising an alcohol and a reduced coenzyme Q10 in the crystallization unit;

adding a reduced coenzyme Q10 Form II crystal as a seed crystal to the mixed solution; and precipitating a reduced coenzyme Q10 Form II crystal in the mixed solution after adding the seed crystal, wherein the precipitating comprises controlling a temperature with the temperature adjustment unit based on a turbidity change rate obtained by the turbidity detection unit.

2. The method according to claim 1, wherein controlling the temperature comprises varying at least one of a temperature and a cooling rate of the mixed solution based on a predetermined range and a measurement value of the turbidity change rate.

3. The method according to claim 2, wherein the predetermined range is a range determined based on a change rate of formazin turbidity (FTU), and the predetermined range is set within a range of 2 to 45 FTU/min in a period during which FTU shifts from 1,000 to 10,000.

4. The method according to claim 1, wherein the alcohol is a monohydric alcohol having 1 to 5 carbon atoms.

5. The method according to claim 4, wherein the monohydric alcohol having 1 to 5 carbon atoms is ethanol.

6. The method according to claim 1, wherein the alcohol is an alcohol of 95% or more by weight based on a total amount of water and alcohol.

7. A crystallizer for a reduced coenzyme Q10 Form II crystal, comprising:

a crystallization unit capable of accommodating a mixed solution containing an alcohol and a reduced coenzyme Q10;

a turbidity detection unit for detecting a turbidity change rate of the mixed solution accommodated in the crystallization unit;

a temperature adjustment unit capable of adjusting a temperature inside the crystallization unit; and a control unit configured to increase the temperature of the mixed solution and/or decrease a cooling rate of the mixed solution when the turbidity change rate of the mixed solution obtained by the turbidity detection unit is greater than a predetermined range, and configured to decrease the temperature of the mixed solution and/or increase the cooling rate of the mixed solution when the turbidity change rate of the mixed solution obtained by the turbidity detection unit is smaller than the predetermined range.

8. The crystallizer according to claim 7, wherein the predetermined range is a range determined based on a change rate of formazin turbidity (FTU), and the predetermined range is set within a range of 2 to 45 FTU/min in a period during which FTU shifts from 1,000 to 10,000.

9. The method according to claim 2, wherein the alcohol is a monohydric alcohol having 1 to 5 carbon atoms.

10. The method according to claim 9, wherein the monohydric alcohol having 1 to 5 carbon atoms is ethanol.

11. The method according to claim 10, wherein the alcohol is an alcohol of 95% or more by weight based on a total amount of water and alcohol.

12. The method according to claim 3, wherein the alcohol is a monohydric alcohol having 1 to 5 carbon atoms.

13. The method according to claim 12, wherein the monohydric alcohol having 1 to 5 carbon atoms is ethanol.

14. The method according to claim 13, wherein the alcohol is an alcohol of 95% or more by weight based on a total amount of water and alcohol.

* * * * *